United States Patent [19]

Carpenter et al.

[11] Patent Number: 5,643,314
[45] Date of Patent: Jul. 1, 1997

[54] SELF-EXPANDING STENT

[75] Inventors: Kenneth W. Carpenter, Del Mar; Leo R. Roucher, Jr., Escondido; Eugene J. Jung, Jr., San Diego, all of Calif.

[73] Assignee: Navius Corporation, San Diego, Calif.

[21] Appl. No.: 557,725

[22] Filed: Nov. 13, 1995

[51] Int. Cl.⁶ .................................................. A61M 29/00
[52] U.S. Cl. ........................... 606/198; 623/1; 623/12; 128/898
[58] Field of Search ................... 623/1, 12; 606/108, 606/191, 194, 195, 198, 200; 128/898, 899

[56] References Cited

U.S. PATENT DOCUMENTS

| | | |
|---|---|---|
| 3,278,176 | 10/1966 | Abolins . |
| 3,842,441 | 10/1974 | Kaiser . |
| 4,214,587 | 7/1980 | Sakura, Jr. . |
| 4,434,797 | 3/1984 | Silander . |
| 4,512,338 | 4/1985 | Balko et al. . |
| 4,553,545 | 11/1985 | Maass et al. . |
| 4,732,152 | 3/1988 | Wallsten et al. . |
| 4,733,665 | 3/1988 | Palmaz . |
| 4,739,762 | 4/1988 | Palmaz . |
| 4,740,207 | 4/1988 | Kreamer . |
| 4,776,337 | 10/1988 | Palmaz . |
| 4,793,348 | 12/1988 | Palmaz . |
| 4,800,882 | 1/1989 | Gianturco . |
| 4,856,516 | 8/1989 | Hillstead . |
| 4,878,906 | 11/1989 | Lindemann et al. . |
| 4,886,062 | 12/1989 | Wiktor . |
| 4,907,336 | 3/1990 | Gianturco . |
| 4,913,141 | 4/1990 | Hillstead . |
| 4,969,458 | 11/1990 | Wiktor . |
| 5,019,090 | 5/1991 | Pinchuk . |
| 5,344,426 | 9/1994 | Lau et al. ........................ 623/1 |
| 5,383,892 | 1/1995 | Cardon et al. ................... 623/1 |
| 5,441,515 | 8/1995 | Khosravi et al. ................ 623/1 |
| 5,449,373 | 9/1995 | Pinchasik et al. ............. 623/12 |

*Primary Examiner*—Michael Powell Buiz
*Assistant Examiner*—William W. Lewis
*Attorney, Agent, or Firm*—Nydegger & Associates

[57] ABSTRACT

The present invention provides a self-expanding stent for insertion into an artery or other internal vessel. The stent is formed from a series of radial bands each formed with overlapping first and second ends. The overlap between the first and second ends is variable, allowing each band to move between a contracted configuration and an expanded configuration. The first and second ends of each band are both formed to include a tab which is folded to hold the first and second end against the band. The bands are distributed along a common axis to form a cylinder and interconnected by a pair of elongated strips. In use, the stent is placed over a balloon catheter and compressed to adopt the contracted configuration. The balloon catheter and stent are then advanced through a placement catheter and to a target site where the balloon is partially inflated to free the stent for self-expansion. The balloon may then be more fully inflated to further expand any of the radial bands in the stent. The balloon is then deflated and removed, leaving the expanded stent to support that target site.

9 Claims, 3 Drawing Sheets

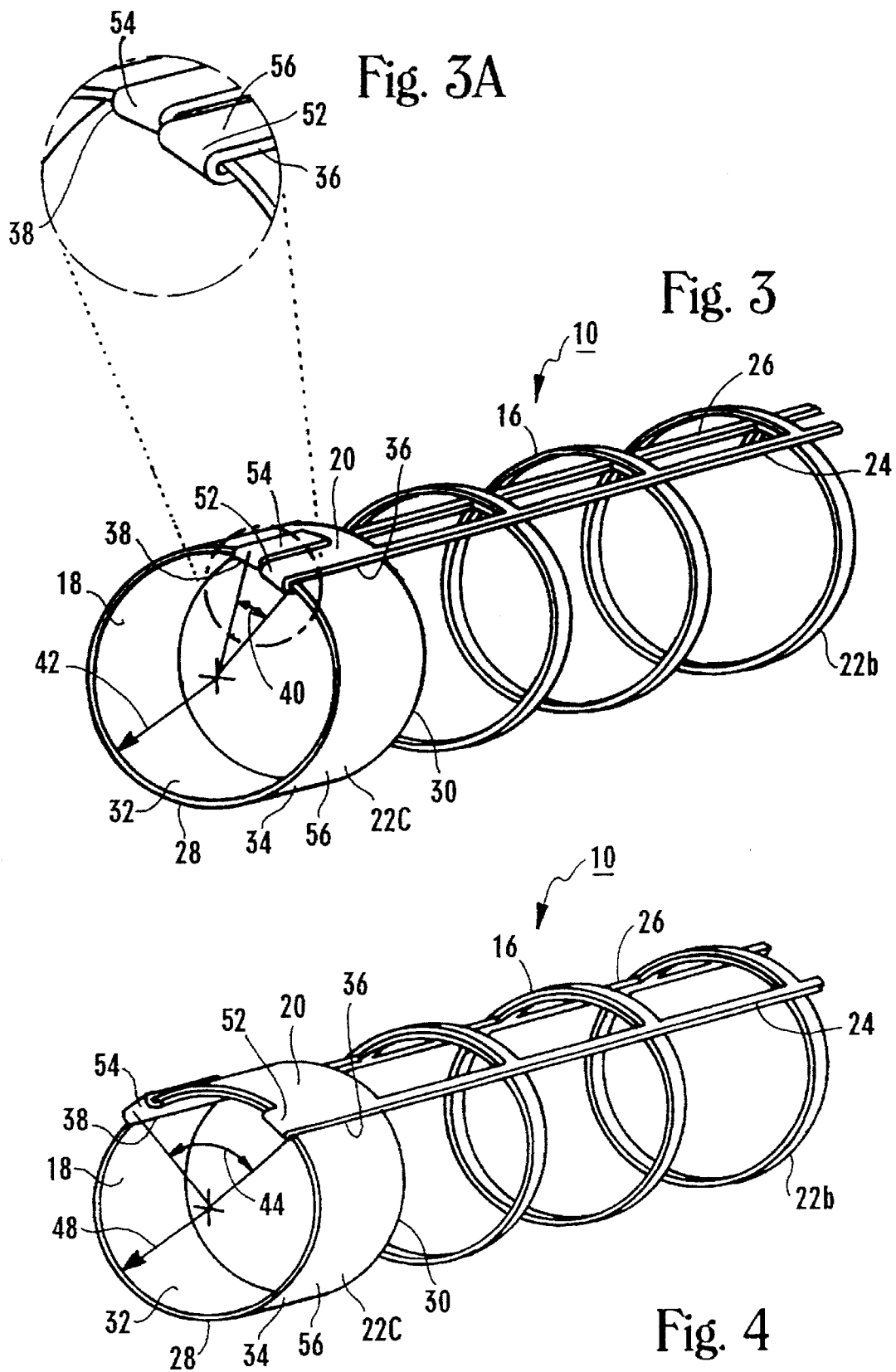

5,643,314

SELF-EXPANDING STENT

FIELD OF THE INVENTION

The present invention pertains generally to devices which are used for treatment of weakened or clogged arteries and other internal vessels. More specifically, the present invention pertains to devices which can be expanded within an artery or other vessel to prevent occlusion of the vessel. The present invention is particularly, but not exclusively, useful as a self-expandable stent for insertion into an artery or vessel to support the vessel wall.

BACKGROUND OF THE INVENTION

The use of stents within vessels, such as arterial vessels, is well known. Generally, devices of this type are inserted into a vessel to support the vessel wall, and thus prevent the wall from collapsing and occluding the vessel. Alternatively, in a procedure commonly referred to as vascular repaving, stents may be inserted into a weakened portion of a vessel to prevent internal pressure within the vessel from causing the vessel wall to rupture. Stents may, therefore, be useful whenever a vessel wall has become weakened (such as by disease) or when the vessel becomes clogged (such as by the buildup of plaque), or whenever surrounding tissue (such as a tumor) is applying pressure to the outside of a vessel which may cause the vessel to collapse.

The benefits associated with the use of stents has resulted, not surprisingly, in the increased use of stents to treat an ever increasing number of maladies. As a result, a wide variety of differing stent designs have been developed, each of which may be more, or less, appropriate for the treatment of a particular condition. A contributing factor to the proliferation of differing stent types has been the problematic conditions faced as part of the design and fabrication of a beneficial stent. For example, it is readily appreciated that the operational environment into which a stent is to be placed may vary widely from the idealized conditions of a laboratory. Specifically, the vessel into which the stent is to be placed may be curved or otherwise tortuous. In such cases, insertion of an inflexible stent may be undesirable or even impossible. This particular difficulty is often avoided by the use of a shorter stent, or even a series of shorter stents. In either case, however, the treatment may be complicated or the efficacy of the treatment may be reduced.

Tapered vessels present another aspect of stent design which can be of concern. Tapered vessels, are of course, not uncommon and may even occur in combination with the curved vessel discussed in the preceding section. In cases which tapered vessels, the use of a stent which cannot conform to the changing diameter of the vessel may be problematic. Once again, the use of a series of shorter stents is possible, but this necessarily complicates the course of treatment.

The particular treatment site may also subject the stent to a relatively large compressive load. In such cases the use of a stent which recoils under the load would be inappropriate. The solution for many cases of this type is the utilization of a stronger, or more robust, stent. The use of a stronger stent may not be possible, however, if the stent is required to provide a high degree of flexibility such as when placement within a curved or tapered vessel is required.

Practice has also shown that the use and placement of stents in small vessels is particularly difficult. More specifically, at present, most stents are designed to be delivered in an unexpanded state and then expanded, in-situ, to support the vessel at the target site. In small vessels (generally those with a diameter of less than three millimeters), there may not be adequate room to allow passage of the stent. This may be so even with the stent in its unexpanded state. The use of smaller stents is possible, but may in itself be difficult if the stent is not strong enough to support the intended compressive load.

In light of the above, it is an object of the present invention to provide a vascular stent which can be inserted into a vessel to support the vessel wall. Another object of the present invention is to provide a vascular stent with can withstand a relatively large compressive load without recoiling. Another object of the present invention is to provide a vascular stent with can be inserted into relatively small vessels. Still another object of the present invention is to provide a vascular stent which expands iso-concentrically to more nearly replicate the original lumen of a vessel. Yet another object of the present invention is to provide a vascular stent which can be utilized in a curved or tapered vascular segment. Still another object of the present invention is to provide a vascular stent which is relatively easy to manufacture, simple to operate and comparatively cost effective.

SUMMARY OF THE PREFERRED EMBODIMENTS

The present invention provides a self-expanding stent for placement into an artery or other vessel within a patient. Structurally, the present invention includes a series of radial bands which are each formed from a resilient and biocompatible material, such as stainless steel. Each radial band is formed to have a first radial edge and a second radial edge. Between these first and second radial edges, each radial band is formed with an inner surface and an outer surface.

Importantly, each radial band is formed to be non-continuous, but to still establish a substantially circular shape. To do this, each radial band has a first end and a second end which partially overlap each other so that a portion of the inner surface of each radial band overlays and contiguously contacts a portion of the outer surface of the same radial band. Thus, the first end of the radial band is free to move along a path over the outer surface of the radial band which is substantially concentric with the path of the second end of the radial band as it moves over the inner surface of the radial band. The movements of the first end and second end of the radial band along their respective concentric paths create an overlap region between them which is able to increase or decrease. Functionally, this allows the radial band to move iso-concentrically between a contracted configuration having a first diameter and an expanded configuration having a second diameter. The resilient material used to form each radial band biases the iso-concentric movement of the bands. More specifically, it may be appreciated that, absent some restraint, each band will iso-concentrically self-expand until the band has nearly reached the expanded configuration.

For the purposes of the present invention, some of the radial bands are formed as locking radial bands. One such locking radial band being a distal band which is formed with a first tab and a second tab. Both the first tab and the second tab of the distal band are positioned to project from its first radial edge. Further, the first tab is positioned to be adjacent to the first end of the locking radial band and the second tab is positioned to be adjacent to the second end of the distal locking radial band. The first tab is then folded radially inward and under the inner surface to form a clasp which holds the first end of the distal locking radial band against its own outer surface. This connection establishes the substantially circular shape of the locking radial band. In a similar fashion, the second tab at the second end of the distal band is folded radially outward and over the outer surface of the distal locking radial band. This connection also forms a clasp. This clasp, however, holds the second end of the distal locking radial band against its own inner surface. Importantly, the clasps formed by the first tab and the second tab maintain the ability of the first end and the second end of the locking radial band to move along their respective concentric paths. In this fashion, the ability of the locking radial band to move iso-concentrically between a contracted configuration and an expanded configuration, by changing the overlap region between the first end and second end of the locking radial band, is preserved.

A structure and cooperation of structure similar to the distal locking radial band is established for another of the locking bands which is at the opposite end of the stent from the distal locking radial band. This other locking radial band is therefore, referred to as the proximal locking radial band.

For a preferred embodiment of the present invention, the first tab of both the distal and proximal locking radial bands is formed with a protrusion. The protrusion is positioned to face the inner surface of the respective locking radial band when the first tab is folded radially inward and under the inner surface. In cooperation with the protrusion on the first tab, the present invention includes a series of detents which are formed in the inner surface of the distal and proximal locking radial bands. The detents are shaped to receive the protrusion included on the first tab and are positioned at a predetermined radial position on the inner surface. As a result, as the first end of the respective locking radial bands moves concentrically over the outer surface of the locking radial band to expand the locking radial band, the protrusion of the first tab sequentially engages each of the detents that are formed on the inner surface of the band. The engagement between the protrusion of the first tab and each of the detents formed on the inner surface provides a locking mechanism which allows the locking radial band to expand (by sequentially engaging each successive detent). This locking mechanism, however, tends to prevent subsequent contraction of the stent. Preferably, the detents included on the inner surface of the respective distal and proximal locking radial bands are positioned to provide the locking mechanism only as the locking radial band nears and reaches the fully expanded configuration.

In a similar fashion, the second tab that is included on both the distal and proximal locking radial bands is also preferably formed with a protrusion. Specifically, the protrusion on the second tab is positioned to face the outer surface of the locking radial band when the second tab is folded radially outward and over the outer surface. In cooperation with the protrusion included on the second tab, at least one detent is formed in the outer surface of each of the locking radial bands. The detent that is included in the outer surface is shaped to receive the protrusion on the second tab and is positioned at a predetermined radial position on the outer surface. Specifically, the radial position of the detent on the outer surface brings the protrusion on the second tab into engagement with the detent as the locking radial band reaches the contracted configuration. Thus, the engagement between the protrusion of the second tab and the detent formed on the outer surface provides a locking mechanism which holds the locking radial band in the contracted configuration until an adequate force is applied to release the locking mechanism which then permits the stent to expand.

The proximal and distal radial bands, together with each of the radial bands that are positioned therebetween, are distributed along a common axis in a substantially parallel array. In effect, this array of radial bands forms an elongated cylinder having an inner surface (corresponding to the inner surface of each radial band) and an outer surface (corresponding to the outer surface of each radial band). Generally, for the purposes of the present invention, the number of radial bands used to form the cylinder, as well as the spacing between the radial bands within the cylinder, may be varied to produce stents of varying dimensions. Between the distal radial band and the proximal radial band, the present invention preferably includes five or ten radial bands. In cases for the longer stents where as many as ten radial bands can be included between the distal radial band and the proximal radial band, an additional locking radial band may also be included at the center of the cylinder.

The present invention also includes a first elongated strip and a second elongated strip. The first elongated strip and second elongated strip are positioned to span the elongated cylinder with the first strip being connected to the first end of each radial band and the second strip being connected to the second end of each radial band. Structurally, the first and second elongated strips provide an interconnection between the series of radial bands which help to maintain the position of each radial band within the elongated cylinder.

The ability of each the radial bands to vary iso-concentrically in diameter, by changing the overlap between the first end and second end of the radial bands, allows the cylinder to move between contracted configuration having a first diameter and an expanded configuration having a second diameter. More specifically, it may be appreciated that a compressive force of sufficient magnitude applied to the outer surface of the elongated cylinder will cause each of the radial bands to compress by increasing the overlap between the first end and second end of the radial band. Once the compressive force is released, however, the resilient nature of each of radial bands causes the cylinder to expand, decreasing the overlap between the first end and second end of each radial band. Importantly, when each of the radial bands is configured at, or near, the contracted or expanded configurations, the first strip and second strip are in close proximity to each other. The close proximity of the first strip and second strips allows the cylinder to easily bend, or flex, along an axis defined by the first and second strips. Importantly, the flexibility of the elongated cylinder allows the device to be advanced through curving or otherwise tortuous vessels. Additionally, the flexibility of the elongated cylinder allows the device to be expanded to support curved vessels.

Operationally, the stent of the present invention is first positioned to surround a portion of an inflatable balloon catheter. The stent, with the balloon catheter inside, is then compressed until each of the radial bands has reached the contracted configuration. At this diameter, the protrusion included in the second tab of each locking radial band engages the detent formed in the locking radial band's outer surface to lock the locking radial bands in their contracted configuration. This also locks the stent over the balloon catheter. A placement catheter is then inserted into the patient's body. The placement catheter is formed with a lumen and the stent and balloon are inserted into the lumen and advanced into the patient's body.

Inside of the patient's body, the stent and balloon catheter are advanced distally out of the placement catheter. The stent and balloon catheter are then advanced until the target site has been reached. With the stent positioned at the target site, the balloon is first partially inflated. This initial partial inflation of the balloon applies an expansive force to the inner surface of each of the radial bands. Additionally, this initial partial inflation overcomes the locking action provided by interaction of the protrusion on the second tab of each locking radial band with the detent formed in the locking radial band's outer surface. When freed from this locking action, the resilient material which form each of the radial bands causes the radial bands to undergo an initial expansion. The initial expansion causes each of the radial bands to expand until the expanded configuration is nearly reached. Once the initial expansion is complete, the balloon can be further inflated to further expand each of the radial bands. In particular, each of the distal and proximal locking radial bands will generally be expanded until the protrusion on the first tab of the locking radial band has engaged with one of the detents that are formed in the inner surface of the locking radial band. As indicated above, depending on which detent is engaged, the stent will assume either a partially or a fully expanded configuration. Subsequently, the balloon may be deflated and removed or reinflated to further expand specific partially expanded locking radial bands within the stent. As can be easily appreciated, differential expansion of the locking radial bands allow the stent to adapt to tapered or otherwise irregular vessels. In all cases, with the expanded stent positioned to support the vessel wall at the target site, the balloon is deflated and the balloon and placement catheter are withdrawn from the vessel to complete the procedure.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3 is an isometric detail of a segment of the stent of the present invention shown with the stent configured in an expanded configuration;

FIG. 3A is an enlarged detail of the overlap region of FIG. 4;

FIG. 4 is an isometric detail of a segment of the stent of the present invention shown with the stent configured in an intermediate configuration;

DESCRIPTION OF THE PREFERRED EMBODIMENT

Figure 1:
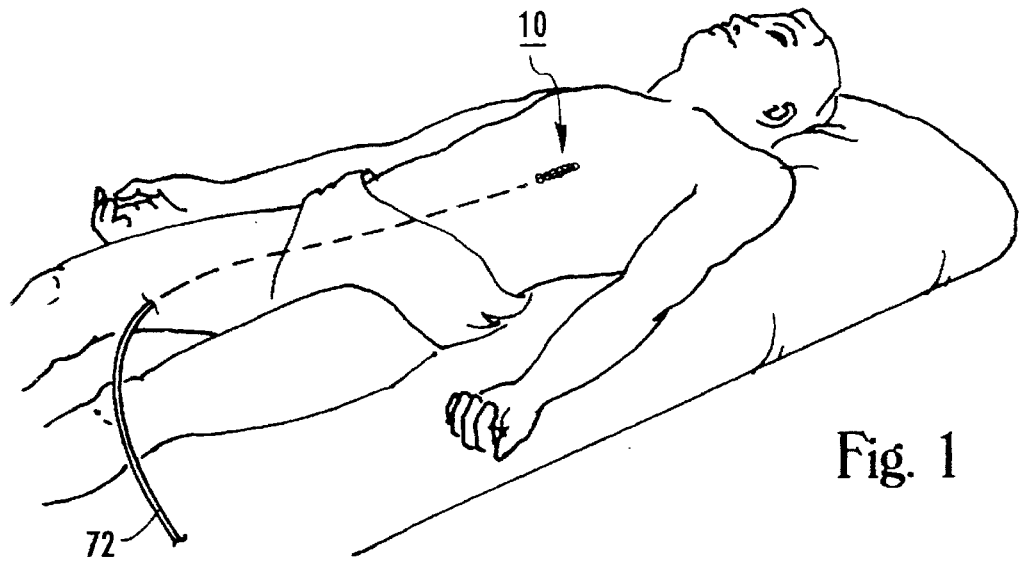
FIG. 1 is a pictorial representation of the stent of the present invention operationally positioned within the vascular system of a patient.

Referring initially to FIG. 1, a self-expanding stent for structurally supporting the wall of a vessel in accordance with the present invention is shown and generally designated 10. For purposes of illustration, the device 10 is shown operationally positioned after being advanced through the femoral artery and toward the heart 14 of the patient 12. It is to be appreciated, however, that the device 10 is useful in vessels throughout the vascular system of patient 12 and may be introduced into the vessel wherever it is most convenient to do so.

Figure 2:
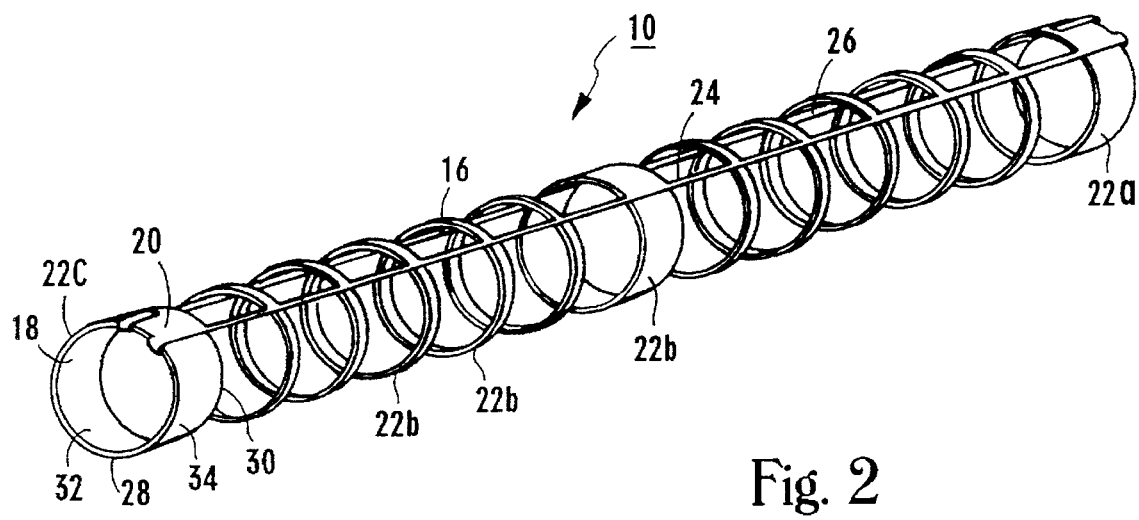
FIG. 2 is an isometric view of the stent of the present invention.

Referring now to FIG. 2, it may be seen that the device 10 is formed as an elongated cylinder 16 having an inner surface 18 and an outer surface 20. The cylinder 16 is formed from a series of radial bands which include distal radial band 22a, intermediate radial bands 22b and proximal radial band 22c. Each radial band 22 is interconnected by a first elongated strip 24 and a second elongated strip 26. It may be appreciated that the elongated cylinder 16 may be covered with thin substrates, such as Rayon fabric, without departing from the present invention.

The structural details of the present invention may be better appreciated by reference to FIG. 3 where it may be seen that proximal radial band 22c is formed to have a substantially circular shape with a first radial edge 28 and a second radial edge 30. Between the first radial edge 28 and the second radial edge 30, each radial band 22 is formed with an inner surface 32 and an outer surface 34. Each radial band 22 is formed to be non-continuous. As a result, each radial band 22 has a first end 36 and a second end 38. The first end 36 and second end 38 of each radial band 22 partially overlap each other so that a portion of the inner surface 32 of each radial band 22 overlays and contiguously contacts the a portion of the outer surface 34 of the same radial band 22. Importantly, the first end 36 of the radial band 22 is moveable over the outer surface 34 of the radial band 22. Similarly, the second end 38 of the radial band 22 is moveable over the inner surface 32 of the radial band 22. The movement of the first end 36 and second end 38 allows the overlap region 40 between the first end 36 of the radial band 22 and the second end 38 of the radial band 22 to increase or decrease. Increasing or decreasing the overlap region 40 of the radial band 22 causes a corresponding increase or decrease in the diameter 42 of the radial band 22.

Figure 5:
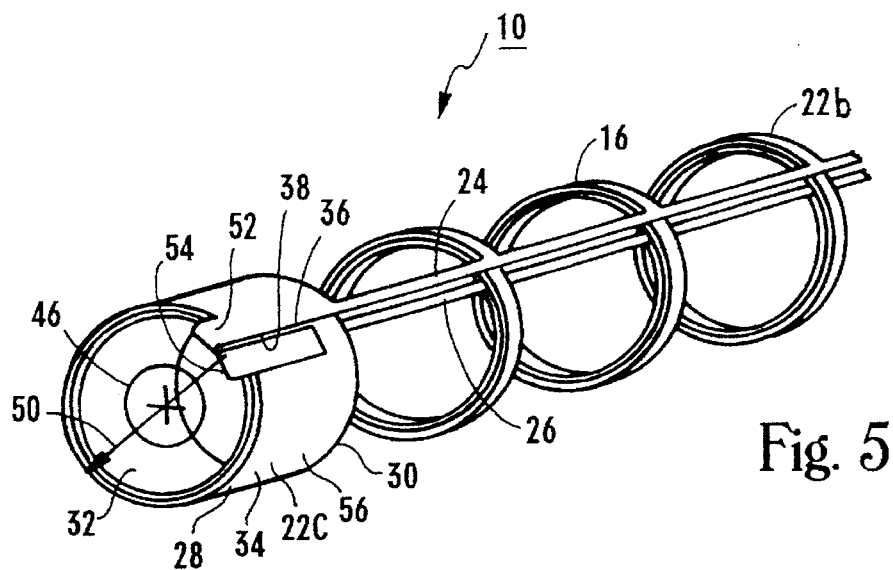
FIG. 5 is an isometric detail of a segment of the stent of the present invention shown with the stent configured in the contracted configuration.

The relationship between the overlap region 40 and the diameter 42 of the radial band 22 may be more easily appreciated by comparison between FIG. 3, where the radial band 22 is shown with in an expanded configuration, FIG. 4, where the radial band 22 is shown in an intermediate configuration, and FIG. 5, where the radial band 22 is shown in a contracted configuration. Specifically, it may be seen that the overlap region 40 of FIG. 3 increases to the overlap region 44 of FIG. 4 and increases still further to the overlap region 46 of FIG. 5. It may also be seen that the diameter 42 of FIG. 3, decreases to diameter 48 in FIG. 4 and decreases still further to diameter 50 of FIG. 5. As the preceding discussion demonstrates, movement of the first end 36 and second end 38 allows the overlap region 40 to be varied and allows the radial band 22 to move between the expanded configuration shown in FIG. 3 and the contracted configuration shown in FIG. 5. The resiliant material used to form each radial band 22 biases the iso-concentric movement of the radial bands 22. More specifically, it may be appreciated that, absent some restraint, each radial band 22 will iso-concentrically self-expand until the radial band 22 has nearly reached the expanded configuration of FIG. 3.

Returning to FIG. 3, it may be seen that the proximal radial band 22c is formed to have a first tab 52 and a second tab 54. The inclusion of first tab 52 and second tab 54 on proximal radial band 22c, identify proximal radial band 22c as a locking radial band 56. For the purposes of the present invention, any number of the radial bands 22 included in the cylinder 16 may be configured as locking radial bands, like locking radial band 56.

First tab 52 and second tab 54 are both positioned to project from the first radial edge 28 of the locking radial band 56. First tab 52 is located to be substantially adjacent to the first end 36 of locking radial band 56 and second tab 54 is located to be substantially adjacent to the second end 38 of locking radial band 56. Both first tab 52 and second tab 54 are folded, with first tab 52 folded radially inward and under inner surface 32 and second tab 54 folded radially outward and over outer surface 34. Functionally, first tab 52 functions as a clasp which holds the first end 36 of locking radial band 56 against the outer surface 34 of locking radial band 56. Similarly, second tab 54 functions as a clasp which holds the second end 38 of locking radial band 56 against the inner surface 32 of locking radial band 56. Importantly, the clasps formed by the first tab 52 and the second tab 54 maintain the ability of the first end 36 and the second end 38 of locking radial band 56 to move over the locking radial band 56. In this fashion, the ability of locking radial band 56 to move iso-concentrically between the contracted configuration of FIG. 5 and the expanded configuration of FIG. 3, by changing the overlap region 40, is maintained.

Figure 6:
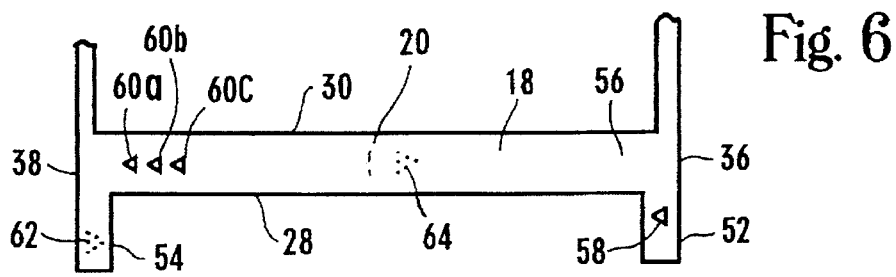
FIG. 6 is a plan view of the locking radial band of the present invention showing the protrusions and detents of the present invention.

The structural details of the locking radial band 56 may be more fully appreciated by reference to FIG. 6 where a representative radial locking band 56 is shown in an unrolled configuration. In FIG. 6, it may be seen that the first tab 52 included in locking radial band 56 is formed with a protrusion 58. The protrusion 58 is positioned to face the inner surface 32 of locking radial band 56 when the first tab 52 is folded radially inward and under the inner surface 32. In cooperation with the protrusion 58, the present invention includes a series of detents 60a, 60b and 60c formed in the inner surface 32 of the locking radial band 56. The detents 60a, 60b and 60c are shaped to receive the protrusion 58 and are positioned at predetermined radial positions on the inner surface 32. As a result, as the first end 36 of the locking radial band 56 moves over the outer surface 34 to expand the locking radial band 56, the protrusion 58 sequentially engages each of the detents 60a, 60b and 60c. The engagement between the protrusion 58 and each of the detents 60a, 60b and 60c provides a locking mechanism which allows locking radial band 56 to expand (by sequentially engaging each successive detent 60a, 60b and 60c) but tends to prevent subsequent contraction. Preferably, the detents 60a, 60b and 60c are positioned to provide the locking mechanism only as the locking radial band 56 nears and reaches the fully expanded configuration of FIG. 3.

As discussed in the preceding paragraphs, the combination of protrusion 58 and detents 60a, 60b, 60c provide a locking mechanism for holding locking radial band 56 in the expanded configuration or near expanded configuration. It may be appreciated however, that the use of protrusions, like protrusion 58 and detents, like detents 60a, 60b, 60c to form locking mechanisms is not limited to the locking radial bands 56 and similar detents and protrusions may be included in any of the radial bands 22.

For the purposes of the present invention, the second tab 54 included in locking radial band 56 is also preferably formed with a protrusion 62. The protrusion 62 is positioned to face the outer surface 34 of the locking radial band 56 when the second tab 54 is folded radially outward and over the outer surface 34. In cooperation with the protrusion 62, the present invention includes at least one detent 64 formed in the outer surface 34 of the locking radial band 56. The detent 64, included in the outer surface 34, is shaped to receive the protrusion 62 included on the second tab 54 and is positioned at a predetermined radial position on the outer surface 34. The radial position of the detent 64 included on the outer surface 34 brings the protrusion 62 and the detent 64 into engagement as the locking radial band 56 reaches the contracted configuration of FIG. 5. The engagement between the protrusion 62 and the detent 64 provides a locking mechanism which holds the locking radial band 56 in the contracted configuration of FIG. 5 until an adequate force is applied to release the locking mechanism and allow expansion of the locking radial band 56.

Returning to FIG. 3, it may be seen that each radial band 22 is distributed along a common axis to form the elongated cylinder 16. Within the elongated cylinder 16, each first end 36 of each radial band 22 is interconnected by the first elongated strip 24. Additionally, each second end 38 of each radial band 22 is interconnected by the second elongated strip 26. Importantly, when the device 10 is configured into the expanded configuration shown in FIG. 3 or the contracted configuration shown in FIG. 5, first elongated strip 24 is positioned to be relatively close to second elongated strip 26. As a result, the elongated cylinder 16 is free to flex along an axis defined by first elongated strip 24 and second elongated strip 26. The ability of the elongated cylinder 16 to flex along the axis defined by first elongated strip 24 and second elongated strip 26 allows the device 10 to be inserted through curved or winding vessels. Additionally, the ability of the elongated cylinder 16 to flex along the axis defined by first elongated strip 24 and second elongated strip 26 allows the device 10 to be expanded to support curved or winding vessels.

The device 10 of the present invention may be preferably fabricated within a range of diameters and overall lengths. Specifically devices which range in diameter from 1.0 to 3.0 millimeters and range in length from ten to forty millimeters have been found to be preferable. The diameter of a given device 10 is determined, of course, by the length between the first end 36 and the second end 38 of each band 22. The overall length, however, depends on the number of radial bands 22, the width between the first radial edge 30 and the second radial edge 32 of each band 22, and the spacing between the radial bands 22. Generally, shorter devices may be fabricated using fewer radial bands 22. For instance, a first preferred embodiment of the present invention include a sequence of seven radial bands 22 of which two, the distal radial band 22a and the proximal radial band 22c are configured as locking radial bands 56. Alternatively a second, longer, preferred embodiment of the present invention includes a sequence of thirteen radial bands 22 of which two, the distal radial band 22a and the proximal radial band 22c are configured as locking radial bands 56. It will be appreciated that even longer embodiments with additional radial bands 22 are envisioned by the present invention. Structurally, longer sequences of radial bands may require additional support. Therefore, in cases where longer sequences of radial bands 22 are included, it may be desirable to configure one of more of the radial bands to have an increased width between the first radial edge 30 and the second radial edge 32. For instance, the radial band 22 positioned at the center of the device 10 of FIG. 2 features an increased width of this nature. It may also be desirable to provide additional interconnections between one or more of the radial bands 22 when long sequences are utilized.

In general, many methods may be utilized for the construction of the device 10 of the present invention. Practice has shown however, that it is highly practical to fabricate the device 10 by photo-chemical milling of a flat sheet of stainless steel. The photo-chemical milling may be used to produce the combination of radial bands 22, first elongated strip 24 and second elongated strip 26 in an unrolled configuration. The unrolled sheet is then rolled to form the elongated cylinder 16 of the present invention.

Operation

Figure 7:
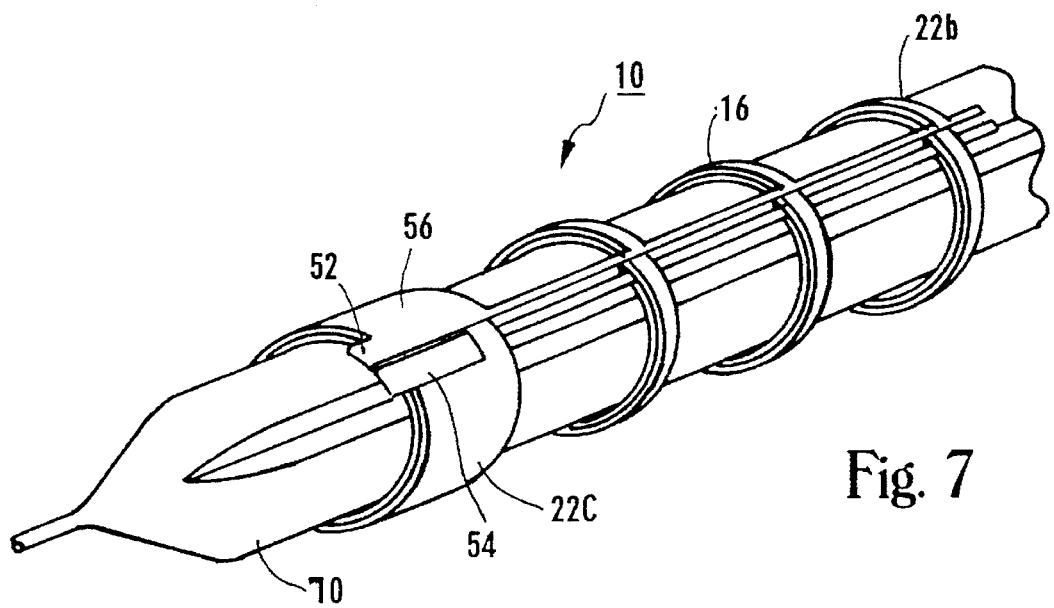
FIG. 7 is an isometric detail of a segment of the stent of the present invention shown positioned over a segment of an inflatable balloon catheter with the balloon shown in a deflated configuration.

Insertion of the device 10 into the vascular system (or other part of the body) begins, as shown in FIG. 7, by placement of the device 10 over an inflatable balloon catheter 70. Once the device is positioned over the inflatable balloon 70, a compressive force is applied to each of the radial bands 22. The compressive force causes each of the radial bands 22 to move iso-concentrically to adopt the contracted configuration of FIG. 5. As the radial bands 22 adopt the contracted configuration of FIG. 5, the protrusion 62 of each locking radial band 56 engages the detent 64 included in the same locking radial band 56, locking the locking radial band 56 in the contracted configuration of FIG. 5. The locking action of the locking radial bands 56 holds the device in position over the inflatable balloon 70 in a manner as best seen in FIG. 7.

Once the device 10 has been configured in the contracted configuration of FIG. 5, and locked around the inflatable balloon 70, a placement catheter (such as the placement catheter 72, shown in FIG. 1) is inserted into a vessel where the device 10 is to be deployed. The device 10 and balloon 70 are then advanced through the placement catheter and into the vessel and towards the target site. Once the target site has been reached, the balloon 70 is partially inflated. The partial inflation of the balloon unlocks each of the locking radial bands 56 by removing the protrusion 62 from the detent 64 of the locking radial band 56.

Once the locking radial bands 56 are unlocked, the resilient material of the radial bands 22 causes the radial bands 22 to self-expand from the contracted configuration of FIG. 5 to reach a nearly expanded configuration, such as the intermediate configuration shown in FIG. 4. The balloon 70 may then be more fully inflated to further expand each of the radial bands 22. In particular, each radial band 22 may be expanded until the protrusion 58 engages detent 60a, 60b or 60c. Importantly, each radial band 22 may be individually expanded to reach an individual degree of expansion. In this fashion, the device 10 may be adapted to support tapered or otherwise irregular vessels. Once the device 10 has been properly expanded, the balloon 70 may be deflated and the balloon 70 and placement catheter may be removed, completing the procedure.

In some cases, internal pressure within a vessel may exceed the strength of a particular vascular segment. In such cases, the present invention may be reconfigured to provide a reinforcing stent adding a thin layer of material, such as Rayon, over the elongated cylinder 16. Insertion of the modified device generally follows the operational sequence outlined in the preceding paragraphs.

While the particular expandable stent as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A self-expanding stent for placement in a vessel which comprises:

a plurality of radial bands, each said band having a first end and a second end with said first end overlapping said second end, said first end being moveable relative to said second end to iso-concentrically reconfigure each band between a contracted configuration having a first diameter and an expanded configuration having a second diameter, each said band being biased to expand from said first diameter to nearly said second diameter with said bands disposed about a common axis;

means for interconnecting each said band to an adjacent said band;

means for locking each said radial band in said expanded configuration; and means for locking each said radial band in said contracted configuration.

2. A self-expanding stent as recited in claim 1 wherein said means for interconnecting each said band to an adjacent said band includes a first elongated strip, said first elongated strip interconnecting said first end of each said radial band to said first end of an adjacent said band.

3. A self-expanding stent as recited in claim 1 wherein said means for interconnecting each said band to an adjacent said band includes a second elongated strip, said second elongated strip interconnecting said second end of each said radial band to said second end of an adjacent said band.

4. A self-expanding stent as recited in claim 1 wherein said means for locking each said radial band in said expanded configuration includes a projection attached to said first end of a particular radial band and a detent formed in said particular radial band, said projection and said detent positioned to engage when said radial bands are configured in said expanded configuration.

5. A self-expanding stent as recited in claim 1 wherein said means for locking each said radial band in said contracted configuration includes a projection attached to said second end of a particular radial band and a detent formed in said particular radial band, said projection and said detent positioned to engage when said radial bands are configured in said contracted configuration.

6. A self-expanding stent as recited in claim 1 wherein said stent is fabricated as a single piece of stainless steel.

7. A method for placing a self-expanding stent at a target site in a vessel of a patient which comprises the steps of:

providing a self-expanding stent which comprises a plurality of radial bands, at least one of said bands being a locking radial band, each said band having a first radial edge and a second radial edge, each said band also having a first end and a second end, said first end overlapping said second end to create an overlap region, said first end being moveable relative to said second end to substantially iso-concentrically reconfigure each band between a contracted configuration and an expanded configuration, at least one tab projecting from said first radial edge of each said locking radial band for folding said tab over said locking radial band to hold said first end and said second end of said locking radial band against said locking radial band in said overlap region, means for interconnecting said first end of each said radial band, means interconnecting said second end of each said radial band, and means for selectively locking said locking radial band in said contracted configuration and said expanded configuration;

configuring said stent to said contracted configuration over at least a portion of a balloon catheter;

advancing said expandable stent and said inflatable balloon to said target site in said vessel; and partially inflating said balloon to unlock said radial bands and allow said radial bands to resiliently self-expand.

8. A method as recited in claim 7 which further comprises the step of further inflating said balloon to further expand said radial bands.

9. A method as recited in claim 8 which further comprises the steps of:

deflating said balloon;

repositioning said balloon;

reinflating said balloon to further expand a particular band within said plurality of bands.

* * * * *